(12) United States Patent
Berthiaume et al.

(10) Patent No.: US 9,421,343 B2
(45) Date of Patent: Aug. 23, 2016

(54) METHOD OF USING CATHETER WITH ROTATING PORTION

(75) Inventors: William Berthiaume, Santa Rosa, CA (US); Gianfranco Pellegrini, Santa Rosa, CA (US); Scott Doig, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1580 days.

(21) Appl. No.: 12/754,827

(22) Filed: Apr. 6, 2010

(65) Prior Publication Data

US 2011/0245782 A1 Oct. 6, 2011

(51) Int. Cl.
*A61M 25/01* (2006.01)

(52) U.S. Cl.
CPC ............ *A61M 25/01* (2013.01); *A61M 25/0152* (2013.01)

(58) Field of Classification Search
CPC ............ A61M 25/01; A61M 25/0152; A61M 25/0105; A61M 25/0116; A61M 25/0133
USPC ............ 604/523–539, 95.01–95.05; 600/585, 600/137; 606/108
See application file for complete search history.

(56) References Cited

U.S. PATENT DOCUMENTS

| 4,779,612 | A | * | 10/1988 | Kishi ............................. 600/141 |
| 5,114,403 | A | * | 5/1992 | Clarke et al. ................ 604/95.04 |
| 5,195,990 | A | * | 3/1993 | Weldon ............. A61M 25/0041 604/264 |
| 5,269,757 | A | * | 12/1993 | Fagan et al. ................. 604/95.01 |
| 5,339,833 | A | | 8/1994 | Berthiaume et al. |
| 5,738,630 | A | * | 4/1998 | Suzuki et al. ................. 600/121 |
| 6,027,460 | A | * | 2/2000 | Shturman ..................... 600/585 |
| 6,387,035 | B1 | | 5/2002 | Jung, Jr. et al. |
| 6,540,719 | B2 | | 4/2003 | Bigus et al. |
| 7,635,383 | B2 | | 12/2009 | Gumm |
| 2006/0178560 | A1 | * | 8/2006 | Saadat et al. .................. 600/114 |
| 2009/0204197 | A1 | | 8/2009 | Dorn et al. |

* cited by examiner

*Primary Examiner* — Bhisma Mehta
*Assistant Examiner* — Brandy S Lee

(57) ABSTRACT

A catheter includes a proximal portion and a distal portion, the distal portion including an arcuate portion. The catheter further includes a rotating portion, the rotating portion connecting the proximal portion and distal portion, the rotating portion including a first piece and a second piece, wherein the first piece and second piece create a snap fit. Methods of using the catheter include threading the inserted catheter through the vasculature and allowing the distal portion to freely rotate about an axis defined by the rotating portion responsive to any tortuosity in the vasculature.

11 Claims, 4 Drawing Sheets

METHOD OF USING CATHETER WITH ROTATING PORTION

TECHNICAL FIELD

This invention relates generally to biomedical devices that are used for treating vascular conditions. More specifically, the invention relates to a catheter with a rotating portion.

BACKGROUND OF THE INVENTION

Catheters are commonly used in vascular procedures. The catheter is threaded through the vasculature to a destination and treatment is applied at the destination. The treatment can take many forms, but a common treatment includes stent delivery.

Delivering the catheter to certain destinations can require traversing vasculature with a high degree of tortuosity. This difficulty is often resolved with force, but this force may result in undesirable effects at the location of any force application. This force may be undesirably increased based on any resistance that the catheter has to rotation.

Additionally, accessing certain areas of the vasculature can require several twists and turns, or may otherwise require undesirable access points. For example, entering the vasculature at the femoral artery or vein can be preferable, but practitioners may encounter difficulty passing a catheter tip into the right atrium or through the atrium and into the pulmonary artery.

Therefore, it would be desirable to provide a catheter that overcomes the aforementioned and other disadvantages.

SUMMARY OF THE INVENTION

One aspect of the present invention is a catheter that includes a proximal portion and a distal portion. The distal portion includes an arcuate portion and a rotating portion. The rotating portion connects the proximal portion and distal portion and includes a first piece and a second piece. The first piece and second piece create a snap fit.

Another aspect of the invention provides a method for obtaining proper positioning of a catheter during a medical procedure. The method includes inserting a catheter into a vasculature of a patient. The catheter includes a proximal portion and a distal portion. The distal portion includes an arcuate portion and a rotating portion. The rotating portion connects the proximal portion and distal portion. The rotating portion includes a first piece and a second piece, wherein the first piece and second piece create a snap fit. The method further includes threading the inserted catheter through the vasculature; and allowing the distal portion to freely rotate about an axis defined by the rotating portion responsive to any tortuosity in the vasculature.

The aforementioned and other features and advantages of the invention will become further apparent from the following detailed description of the presently preferred embodiments, read in conjunction with the accompanying drawings, which are not to scale. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Figure 1:
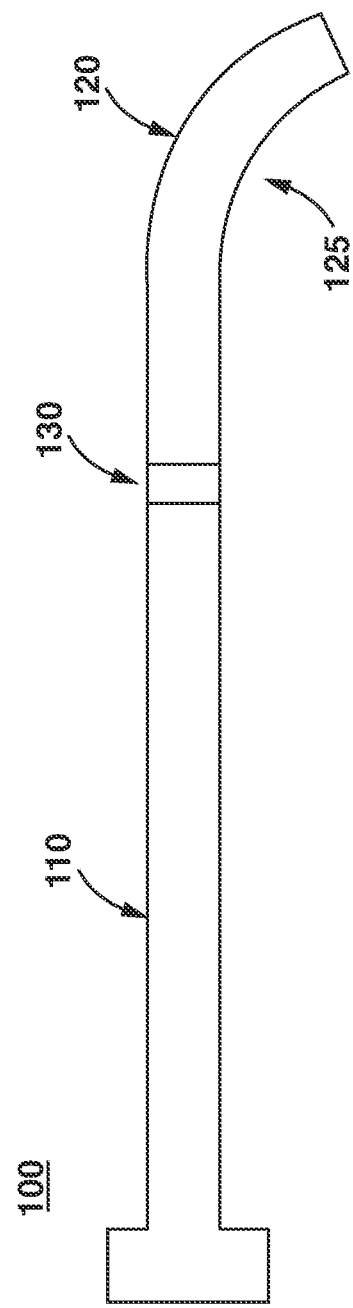
FIG. 1 shows a side view of one embodiment of a catheter in accordance with the present invention.

One aspect of the present invention is a catheter. One embodiment of the catheter, in accordance with the present invention, is illustrated in FIG. 1 at 100. Catheter 100 includes a proximal portion 110 and a distal portion 120. The distal portion 120 includes an arcuate portion 125. The arcuate portion 125 defines at least one radius such that there is no straight axis defined by the length of the arcuate portion 125. In one embodiment, each of the proximal portion 110 and distal portion 120 are integral and are not portions of the same structure.

Figure 2:
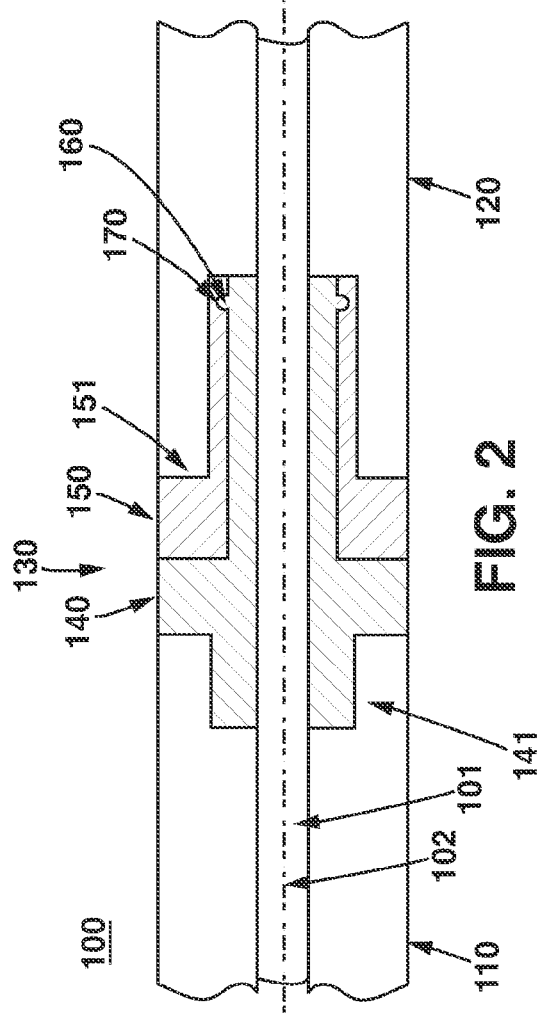
FIG. 2 shows a longitudinal cross-sectional view of the rotating portion of one embodiment of a catheter in accordance with the present invention.

FIG. 2 illustrates aspects of the catheter 100 of FIG. 1 in greater detail. Specifically, catheter 100 includes a rotating portion 130. Rotating portion 130 connects the proximal portion and distal portion when catheter 100 is assembled. Rotating portion 130 includes a first piece 140 and a second piece 150. When assembled, first piece 140 and second piece 150 create a rotating snap fit. In one embodiment, each of the first piece 140 and second piece 150 define a lumen 101 with an axis 102 such that one of the first piece 140 and second piece 150 slides within the other of the pieces to form a connected structure, i.e. a snap fit. In one embodiment, one of the first piece 140 and second piece 150 is slidably received within the other.

Figure 3:
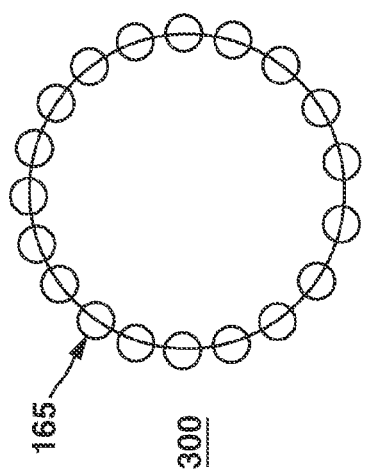
FIG. 3 shows a transverse cross-sectional view of another embodiment of a catheter in accordance with the present invention.

Rotating portion 130 further includes a circumferential protrusion or rib 160 and a circumferential groove or notch 170. The circumferential notch 170 is sized to receive the circumferential rib 160 with a sufficient clearance to permit rotation of the mated parts. In one embodiment, the first piece 140 includes the circumferential notch 170 and the second piece 150 includes the circumferential rib 160. In another embodiment, the first piece includes a circumferential arrangement of bearings and the second piece includes a circumferential notch sized to receive the circumferential arrangement of bearings. In other embodiments, the circumferential rib 160 is a circumferential arrangement of bearings 165, as seen in FIG. 3. The bearings 165 could be ball bearings or other such device. The arrangement may include a cage such that the bearings do not make contact with each other, or in other embodiments, the bearings do make contact with each other. The circumferential rib 160 and circumferential notch 170, in one embodiment, are snap-fitted together to exert sufficient frictional or resistive force against each other as to reduce the risk of disengaging unintentionally in response to axial force. When first piece 140 and second piece 150 are slidably connected to form the snap-fit, the circumferential rib 160 or bearings 165 are mated with the circumferential notch 170 to permit low-friction rotation with a high resistance to longitudinal separation.

Figure 4:
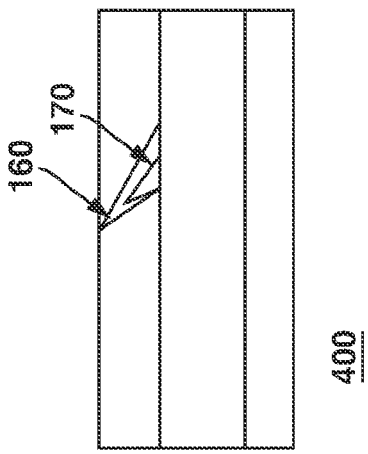
FIG. 4 is a longitudinal cross-sectional view of another embodiment of a catheter in accordance with the present invention.

As illustrated in longitudinal cross-section in FIG. 2, the first piece 140 roughly defines a t-shaped cross section, while second piece 150 roughly surrounds the lower portion of the "t." In one embodiment, the first piece 140 includes a neck portion 141 for attaching to the proximal catheter shaft 110 with a lap joint. The second piece 150 includes a neck portion 151 for attaching to the distal catheter shaft 120 with a lap joint. The first piece 140 and second piece 150 snap-fit together. As used herein, the term snap-fit means any connection that snaps together. Three kinds of snap-fit connections are envisioned, although other snap-fit connections are known—a full cylindrical undercut with mating lip, flexible cantilevered lugs, and spherical undercuts. Other geometric arrangements of the snap fit are possible, including a generally cylindrical arrangement or a more conical shape. Additionally, different arrangements of a circumferential notch and circumferential rib can be used. The resistance of the circumferential rib to compression forces can be configured to allow sufficient deformity to enter the circumferential notch while rendering removal from the notch difficult. Alternatively or additionally, the shape of the circumferential rib and notch can be complementary to resist removal, such as by using an angled and locking arrangement. Such an arrangement is illustrated, partially in FIG. 4.

The devices disclosed herein can be constructed from any biocompatible material, such as stainless steel, medical grade plastics, nitinol or the like. The circumferential rib is advantageously constructed from a material sufficiently flexible to allow insertion into the notch, but sufficiently rigid as to render an accidental separation difficult. Catheters constructed in accordance with these teachings may be, for example, a hypotube made of a biocompatible material such as stainless steel or nitinol. The catheter may or may not be configured to translate along a guidewire. The catheter may be about 120 centimeters to about 300 centimeters long, with a length of about 180 centimeters often being used. The outer diameter of the catheter may range from about 0.010 inches to 0.038 inches. In certain embodiments, the outer diameter of the catheter provides a close sliding fit for a treatment instrument riding thereover, such as an atherectomy catheter, an angioplasty catheter, or a stent delivery catheter. The first and second pieces can be made of any sufficiently flexible material to allow for a snap-fit, such as polyamide or acetal resins, and the material is preferably bio-compatible.

Another aspect of the invention provides a method for obtaining proper position of a catheter during a medical procedure. The method includes inserting a catheter into the vasculature of a patient. In one embodiment, the catheter is substantially as described above, and includes a distal portion having an arcuate portion and being connected to a proximal portion by a rotating portion. The method further includes threading the inserted catheter through the vasculature and allowing the distal portion to freely rotate about an axis defined by the rotating portion responsive to any tortuosity in the vasculature. In one embodiment, the catheter is threaded through a vessel with several bends. In another embodiment, the catheter is threaded through the inferior vena cava into the right atrium of a heart, through the valve into the right ventricle, and from the right ventricle into the pulmonary artery. Threading the catheter into the pulmonary artery can include deflecting the catheter tip off of a wall of the right ventricle, causing the distal portion to rotate respective to the proximal portion as the arcuate portion seeks a least strain energy position during bending. This rotation can assist the practitioner in directing the catheter to the desired destination, as the distal portion rotates relative to the proximal portion freely to achieve a degree of self-steering or self-orienting.

Figure 6:
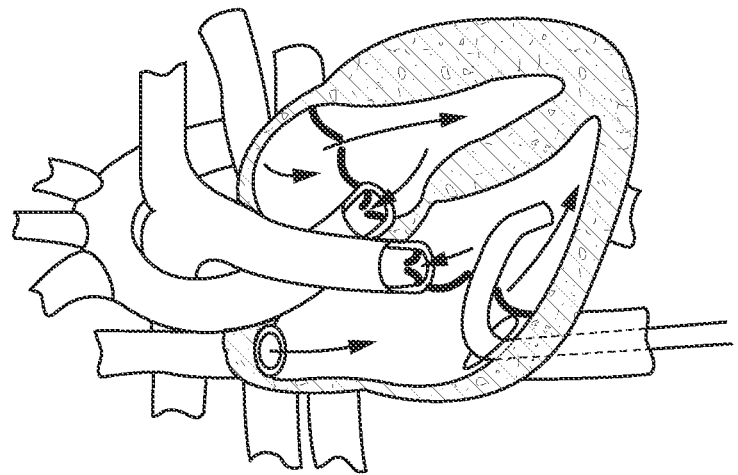
FIGS. 5-8 illustrate the catheter of FIG. 1 passing from the inferior vena cava through the right atrium, tricuspid valve, right ventricle, and into the pulmonary artery.
Figure 5:
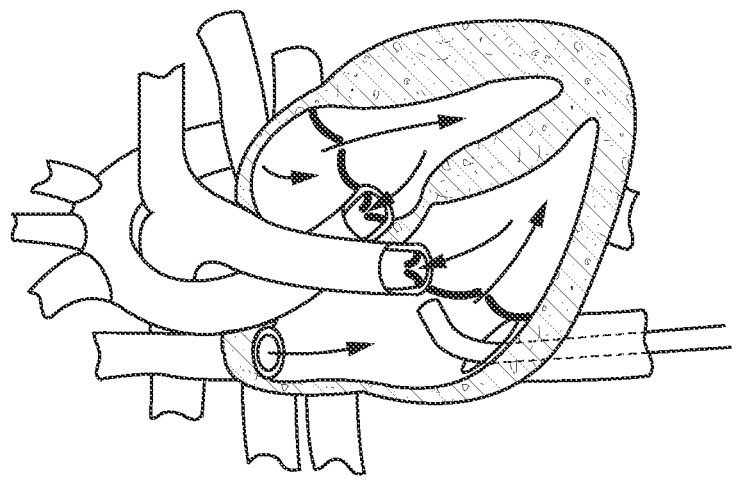
Figure 8:
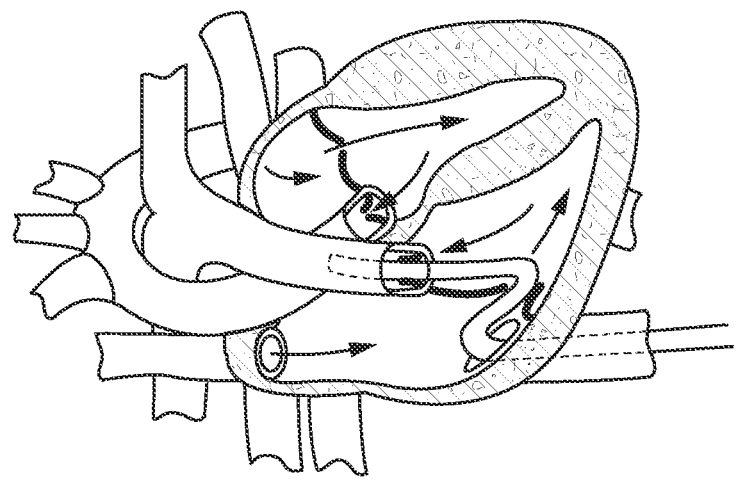
Figure 7:
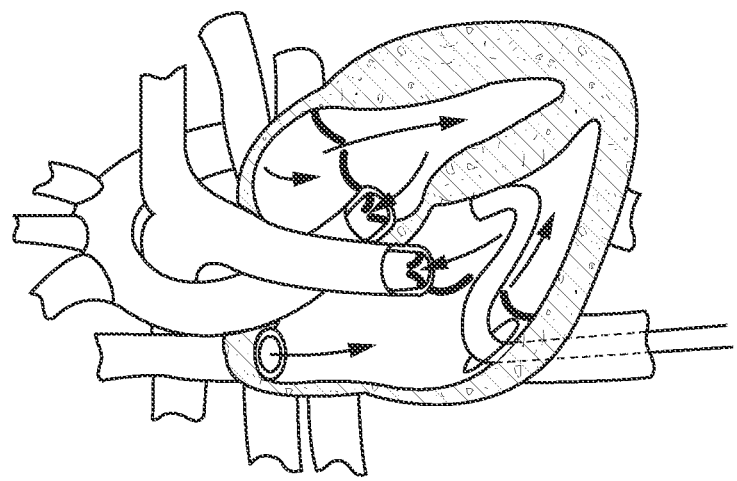

FIGS. 5-8 illustrate a method of using the invention wherein the catheter as described above passes through the inferior vena cava in FIG. 5, and into the right atrium. In FIG. 6, the catheter has traversed the tricuspid valve and entered into the right ventricle. In FIG. 7, the distal tip has rotated relative to the proximal portion based on contact with the wall of the ventricle, and in FIG. 8, the distal portion of the catheter has entered the pulmonary artery. As the distal portion threads through the vasculature, the tip is subjected to strain energy as the tip contacts various aspects of the tissue. The distal portion is able to rotate freely with respect to the proximal portion, and in response to the strain energy, the distal portion rotates to seek the lowest strain energy. Thus, as shown in FIGS. 5-6, the distal portion enters the right atrium and contacts an interior wall of the right atrium, increasing the strain energy and causing the distal portion to rotate relative to the proximal portion in order to reduce or relieve this strain energy. Once the tip has oriented in the least strain energy direction, the clinician can advance the catheter farther in the desired direction, e.g. through the tricuspid valve, by simply pushing the catheter in a distal direction. Further, after passing through the tricuspid valve, as shown in FIGS. 6-7, the distal portion enters the right ventricle and contacts an interior wall thereof, increasing the strain energy and causing the distal portion to again rotate relative to the proximal portion in order to reduce or relieve this strain energy. Once the tip has again oriented in the least strain energy position, the clinician can continue to advance the catheter farther in the desired direction, e.g. into the pulmonary artery. Of course, the clinician will optimally use care to not apply sufficient force to cause trauma to the interior walls of the atrium, or other areas of the vasculature. The distal and proximal portions of the catheter are flexible enough to bend, and may do so to conform to bends in the vasculature. In other words, the distal portion can rotate to seek the least strain energy bending condition without requiring the proximal portion to also rotate, or the entire catheter shaft to twist.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A self-steering catheter for traversing tortuous vasculature in a patient, the catheter having an elongate flexible shaft comprising:
   a flexible proximal shaft portion;
   a rotating portion affixed to the proximal shaft portion and defining an axis; and
   a flexible distal shaft portion affixed to and extending from the rotating portion to a catheter distal end, the distal shaft portion including an arcuate portion;
   wherein the rotating portion is configured to permit the distal shaft portion to rotate freely about the axis in response to the tortuous vasculature without requiring the proximal shaft portion to also rotate or the entire catheter shaft to twist.

2. The self-steering catheter of claim 1 wherein the rotating portion is configured to permit the distal shaft portion to rotate freely about the axis in response to the distal shaft portion contacting the tortuous vasculature.

3. The self-steering catheter of claim 1 wherein the rotating portion is configured to permit the distal shaft portion to rotate freely about the axis in response to the distal shaft portion bending upon contact with the tortuous vasculature.

4. The self-steering catheter of claim 3 wherein the rotating portion is configured to permit the distal shaft portion to rotate freely about the axis to relieve strain energy resulting from the distal shaft portion bending upon contact with the tortuous vasculature.

5. A method for using a self-steering catheter, the method comprising:
inserting a catheter into a vasculature of a patient, the catheter having an elongate flexible shaft including a flexible proximal shaft portion, a flexible distal shaft portion having an arcuate portion, and a rotating portion connecting the proximal and distal shaft portions;
threading the inserted catheter through the vasculature; and
contacting vascular tissue with the distal shaft portion thereby causing the distal shaft portion to freely rotate without requiring the proximal shaft portion to also rotate or the entire catheter shaft to twist.

6. The method of claim 5 wherein the threading comprises:
advancing the catheter through an inferior vena cava into a right atrium of a heart; and
passing the catheter through a heart valve into a pulmonary artery.

7. The method of claim 6 wherein the passing comprises:
deflecting the catheter off an interior wall of the right ventricle based on the advancing.

8. A method for obtaining a proper position of a catheter in a patient during a medical procedure, the method comprising:
receiving a catheter comprising an elongate flexible shaft having a flexible proximal shaft portion freely rotatably connected to a flexible distal shaft portion via a rotating portion, the distal shaft portion including an arcuate portion;
inserting the catheter into a vasculature of the patient; and
deflecting the arcuate portion off of a wall in the vasculature such that the distal shaft portion rotates itself freely with respect to the proximal shaft portion until the distal shaft portion achieves a least strain energy bending condition without requiring the proximal shaft portion to also rotate or the entire catheter shaft to twist.

9. The method of claim 8 further comprising advancing the catheter through a vena cava into a right atrium of the patient wherein the deflecting step comprises deflecting the arcuate portion off of a wall of the right atrium such that the distal shaft portion is directed towards a tricuspid valve.

10. The method of claim 9 further comprising:
advancing the catheter through the tricuspid valve into a right ventricle of the patient; and
deflecting the arcuate portion off of a wall of the right ventricle such that the distal shaft portion is directed towards a pulmonary valve of the patient.

11. The method of claim 10 further comprising:
advancing the catheter through the pulmonary valve into a pulmonary artery of the patient.

\* \* \* \* \*